(12) United States Patent
Aranyi et al.

(10) Patent No.: US 9,717,498 B2
(45) Date of Patent: Aug. 1, 2017

(54) SURGICAL STAPLING APPARATUS

(71) Applicant: Covidien LP, Mansfield, MA (US)

(72) Inventors: Ernest Aranyi, Easton, CT (US);
Kevin Robert Slisz, Old Saybrook, CT (US)

(73) Assignee: Covidien LP, Mansfield, MA (US)

( * ) Notice: Subject to any disclaimer, the term of this patent is extended or adjusted under 35 U.S.C. 154(b) by 668 days.

(21) Appl. No.: 14/169,463

(22) Filed: Jan. 31, 2014

(65) Prior Publication Data
US 2014/0263550 A1 Sep. 18, 2014

Related U.S. Application Data

(60) Provisional application No. 61/779,631, filed on Mar. 13, 2013.

(51) Int. Cl.
*A61B 17/068* (2006.01)
*A61B 17/072* (2006.01)
*A61B 17/00* (2006.01)

(52) U.S. Cl.
CPC *A61B 17/07207* (2013.01); *A61B 2017/0046* (2013.01); *A61B 2017/07271* (2013.01); *A61B 2017/07278* (2013.01)

(58) Field of Classification Search
CPC ...... A61B 17/07207; A61B 2017/0046; A61B 2017/00473; A61B 2017/07271;
(Continued)

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

AU 198654765 9/1986
AU 2002 300 129 6/2005
(Continued)

OTHER PUBLICATIONS

European Search Report dated Jun. 16, 2016, issued in EP Application No. 16155348.
(Continued)

*Primary Examiner* — Hemant M Desai
*Assistant Examiner* — Valentin Neacsu

(57) ABSTRACT

A surgical stapling apparatus (stapler) is provided. A tool assembly includes first and second jaw members. A cartridge assembly includes an actuation sled and a slide. A drive member having a working end is configured to translate through the tool assembly when the first and second jaw members are in a closed configuration. A lock assembly including a latch is movable from a locked position to an unlocked position. The latch is urged to the locked position to engage the working end to prevent distal translation of the drive member through the tool assembly. The slide is configured to move the latch from the locked position to the unlocked position upon installation of an unspent cartridge assembly onto the first jaw member. The slide is movable by the drive member upon actuation of the stapling apparatus to allow the latch to move back to the locked position.

14 Claims, 12 Drawing Sheets

(58) Field of Classification Search
CPC .. A61B 2017/07278; A61B 2017/07285; A61B 2090/0814
USPC ............................................ 227/175.2, 175.3
See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughetti et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |

(56) References Cited

U.S. PATENT DOCUMENTS

| | | |
|---|---|---|
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,706,998 A * | 1/1998 | Plyley ................... A61B 17/072 227/175.2 |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A * | 3/1999 | Bittner ............. A61B 17/07207 227/175.4 |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A * | 6/2000 | Milliman ......... A61B 17/07207 227/175.2 |
| 6,099,551 A | 8/2000 | Gabbay |
| 6,109,500 A * | 8/2000 | Alli .................. A61B 17/07207 227/175.2 |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |

(56) References Cited

U.S. PATENT DOCUMENTS

| | | |
|---|---|---|
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Gerbi et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,945,444 B2 | 9/2005 | Gresham |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielson et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Gillum et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |

(56) References Cited

U.S. PATENT DOCUMENTS

| | | |
|---|---|---|
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton et al. |
| 7,740,160 B2 | 6/2010 | Viola |
| 7,743,960 B2 | 6/2010 | Whitman |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 * | 11/2010 | Baxter, III ........ A61B 17/07207 227/175.1 |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |

(56) References Cited

U.S. PATENT DOCUMENTS

| | | |
|---|---|---|
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica et al. |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffen et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,035 B2 | 12/2011 | Holsten et al. |
| 8,074,858 B2 | 12/2011 | Marczyk et al. |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,901 B2 | 8/2012 | Stopek |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |

(56) References Cited

U.S. PATENT DOCUMENTS

| | | |
|---|---|---|
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillsted |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV et al. |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |

(56) References Cited

U.S. PATENT DOCUMENTS

| | | | |
|---|---|---|---|
| 8,556,151 B2 | 10/2013 | Viola | |
| 8,561,870 B2 | 10/2013 | Baxter, III et al. | |
| 8,561,873 B2 | 10/2013 | Ingmanson et al. | |
| 8,561,874 B2 | 10/2013 | Scirica | |
| 8,567,656 B2 | 10/2013 | Shelton, IV et al. | |
| 8,573,461 B2 | 11/2013 | Shelton, IV et al. | |
| 8,573,463 B2 | 11/2013 | Scirica et al. | |
| 8,573,465 B2 | 11/2013 | Shelton, IV | |
| 8,579,176 B2 | 11/2013 | Smith et al. | |
| 8,579,177 B2 | 11/2013 | Beetel | |
| 8,584,919 B2 | 11/2013 | Hueil et al. | |
| 8,584,920 B2 | 11/2013 | Hodgkinson | |
| 8,590,762 B2 | 11/2013 | Hess et al. | |
| 8,596,515 B2 | 12/2013 | Okoniewski | |
| 8,602,288 B2 | 12/2013 | Shelton, IV et al. | |
| 8,608,045 B2 | 12/2013 | Smith | |
| 8,608,046 B2 | 12/2013 | Laurent et al. | |
| 8,608,047 B2 | 12/2013 | Holsten et al. | |
| 8,613,383 B2 | 12/2013 | Beckman et al. | |
| 8,613,384 B2 | 12/2013 | Pastorelli et al. | |
| 8,616,427 B2 | 12/2013 | Viola | |
| 8,616,430 B2 | 12/2013 | Stopek | |
| 8,627,994 B2 | 1/2014 | Zemlok et al. | |
| 8,628,544 B2 | 1/2014 | Farascioni | |
| 8,631,988 B2 | 1/2014 | Viola | |
| 8,631,989 B2 | 1/2014 | Aranyi et al. | |
| 8,631,991 B2 | 1/2014 | Cropper et al. | |
| 8,632,525 B2 | 1/2014 | Kerr | |
| 8,632,535 B2 | 1/2014 | Shelton, IV et al. | |
| 8,636,187 B2 | 1/2014 | Hueil et al. | |
| 8,636,190 B2 | 1/2014 | Zemlok et al. | |
| 8,636,192 B2 | 1/2014 | Farascioni et al. | |
| 8,636,762 B2 | 1/2014 | Whitman et al. | |
| 8,636,766 B2 | 1/2014 | Milliman et al. | |
| 8,640,940 B2 | 2/2014 | Ohdaira | |
| 8,657,174 B2 | 2/2014 | Yates et al. | |
| 8,657,177 B2 | 2/2014 | Scirica et al. | |
| 8,657,178 B2 | 2/2014 | Hueil et al. | |
| 8,662,371 B2 | 3/2014 | Viola | |
| 8,668,129 B2 | 3/2014 | Olsen | |
| 8,672,206 B2 | 3/2014 | Aranyi et al. | |
| 8,672,208 B2 | 3/2014 | Hess | |
| 8,672,209 B2 | 3/2014 | Crainich | |
| 8,678,263 B2 | 3/2014 | Viola | |
| 8,678,990 B2 | 3/2014 | Wazer et al. | |
| 8,679,155 B2 | 3/2014 | Knodel et al. | |
| 8,684,247 B2 | 4/2014 | Scirica et al. | |
| 8,684,249 B2 | 4/2014 | Racenet et al. | |
| 8,690,039 B2 | 4/2014 | Beardsley et al. | |
| 8,695,865 B2 | 4/2014 | Smith et al. | |
| 8,695,866 B2 | 4/2014 | Leimbach et al. | |
| 8,701,958 B2 | 4/2014 | Shelton et al. | |
| 8,701,959 B2 | 4/2014 | Shah | |
| 8,701,961 B2 | 4/2014 | Ivanko | |
| 8,708,213 B2 | 4/2014 | Shelton, IV et al. | |
| 8,714,429 B2 | 5/2014 | Demmy | |
| 8,715,277 B2 | 5/2014 | Weizman | |
| 8,720,766 B2 | 5/2014 | Hess et al. | |
| 8,721,630 B2 | 5/2014 | Ortiz et al. | |
| 8,727,197 B2 | 5/2014 | Hess et al. | |
| 8,727,200 B2 | 5/2014 | Roy | |
| 8,733,612 B2 | 5/2014 | Ma | |
| 8,740,034 B2 | 6/2014 | Morgan et al. | |
| 8,740,039 B2 | 6/2014 | Farascioni | |
| 2004/0108357 A1 | 6/2004 | Milliman | |
| 2004/0199180 A1 | 10/2004 | Knodel et al. | |
| 2004/0199181 A1 | 10/2004 | Knodel et al. | |
| 2004/0243151 A1 | 12/2004 | Demmy | |
| 2004/0267310 A1 | 12/2004 | Racenet | |
| 2005/0023324 A1* | 2/2005 | Doll | A61B 17/07207 227/175.2 |
| 2005/0067457 A1* | 3/2005 | Shelton, IV | A61B 17/07207 227/175.2 |
| 2005/0103819 A1 | 5/2005 | Racenet | |
| 2005/0178813 A1* | 8/2005 | Swayze | A61B 17/07207 227/176.1 |
| 2005/0189397 A1 | 9/2005 | Jankowski | |
| 2005/0216055 A1 | 9/2005 | Scirica et al. | |
| 2005/0222616 A1* | 10/2005 | Rethy | A61B 17/07207 606/215 |
| 2006/0000867 A1* | 1/2006 | Shelton, IV | A61B 17/07207 227/175.1 |
| 2006/0049229 A1 | 3/2006 | Milliman et al. | |
| 2006/0175375 A1* | 8/2006 | Shelton, IV | A61B 17/07207 227/176.1 |
| 2006/0180634 A1 | 8/2006 | Shelton, IV et al. | |
| 2006/0219752 A1* | 10/2006 | Arad | A61B 17/07207 227/176.1 |
| 2006/0289602 A1 | 12/2006 | Wales et al. | |
| 2007/0029364 A1* | 2/2007 | Kruszynski | A61B 17/072 227/175.2 |
| 2007/0073341 A1 | 3/2007 | Smith et al. | |
| 2007/0084897 A1 | 4/2007 | Shelton, IV et al. | |
| 2007/0102472 A1 | 5/2007 | Shelton, IV | |
| 2007/0102475 A1* | 5/2007 | Ortiz | A61B 17/07207 227/175.2 |
| 2007/0106317 A1 | 5/2007 | Shelton, IV | |
| 2007/0119901 A1 | 5/2007 | Ehrenfels et al. | |
| 2007/0145096 A1 | 6/2007 | Viola et al. | |
| 2007/0170225 A1 | 7/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2007/0179528 A1 | 8/2007 | Soltz et al. | |
| 2007/0194079 A1 | 8/2007 | Hueil et al. | |
| 2007/0194082 A1 | 8/2007 | Morgan et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0041916 A1* | 2/2008 | Milliman | A61B 17/07207 227/175.4 |
| 2008/0078802 A1 | 4/2008 | Hess et al. | |
| 2008/0110961 A1 | 5/2008 | Voegele et al. | |
| 2008/0169328 A1 | 7/2008 | Shelton | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0287987 A1 | 11/2008 | Boyden et al. | |
| 2008/0296346 A1 | 12/2008 | Shelton, IV et al. | |
| 2008/0308602 A1 | 12/2008 | Timm et al. | |
| 2008/0308603 A1 | 12/2008 | Shelton, IV et al. | |
| 2009/0001121 A1 | 1/2009 | Hess et al. | |
| 2009/0001130 A1 | 1/2009 | Hess et al. | |
| 2009/0090763 A1 | 4/2009 | Zemlok et al. | |
| 2009/0090766 A1 | 4/2009 | Knodel | |
| 2009/0209946 A1 | 8/2009 | Swayze et al. | |
| 2009/0242610 A1 | 10/2009 | Shelton, IV et al. | |
| 2009/0255974 A1 | 10/2009 | Viola | |
| 2009/0272787 A1 | 11/2009 | Scirica | |
| 2009/0277949 A1 | 11/2009 | Viola et al. | |
| 2009/0283568 A1 | 11/2009 | Racenet et al. | |
| 2009/0308907 A1 | 12/2009 | Nalagatla et al. | |
| 2010/0012703 A1 | 1/2010 | Calabrese et al. | |
| 2010/0069942 A1 | 3/2010 | Shelton, IV | |
| 2010/0127041 A1 | 5/2010 | Morgan et al. | |
| 2010/0133317 A1 | 6/2010 | Shelton, IV et al. | |
| 2010/0147921 A1 | 6/2010 | Olson | |
| 2010/0147922 A1 | 6/2010 | Olson | |
| 2010/0155453 A1 | 6/2010 | Bombard et al. | |
| 2010/0193566 A1 | 8/2010 | Scheib et al. | |
| 2010/0224668 A1 | 9/2010 | Fontayne et al. | |
| 2010/0249802 A1 | 9/2010 | May et al. | |
| 2010/0252611 A1 | 10/2010 | Ezzat et al. | |
| 2010/0294829 A1 | 11/2010 | Giordano et al. | |
| 2010/0305552 A1 | 12/2010 | Shelton, IV et al. | |
| 2010/0320252 A1 | 12/2010 | Viola et al. | |
| 2011/0006099 A1 | 1/2011 | Hall et al. | |
| 2011/0006101 A1* | 1/2011 | Hall | A61B 17/07207 227/175.2 |
| 2011/0017801 A1 | 1/2011 | Zemlok et al. | |
| 2011/0024477 A1 | 2/2011 | Hall | |

(56) References Cited

U.S. PATENT DOCUMENTS

| | | |
|---|---|---|
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0155781 A1 | 6/2011 | Swensgard et al. |
| 2011/0155784 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0174862 A1 | 7/2011 | Shelton, IV et al. |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0210157 A1 | 9/2011 | Knodel et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0055972 A1 | 3/2012 | Marczyk |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0138660 A1 | 6/2012 | Shelton, IV |
| 2012/0175399 A1 | 7/2012 | Shelton, IV et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199630 A1 | 8/2012 | Shelton, IV |
| 2012/0199632 A1 | 8/2012 | Spivey et al. |
| 2012/0203247 A1 | 8/2012 | Shelton, IV et al. |
| 2012/0211542 A1 | 8/2012 | Racenet |
| 2012/0217282 A1 | 8/2012 | Beetel |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur et al. |
| 2012/0241497 A1 | 9/2012 | Mandakolathur et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255985 A1 | 10/2012 | Ma et al. |
| 2012/0255986 A1 | 10/2012 | Petty et al. |
| 2012/0273547 A1 | 11/2012 | Hodgkinson et al. |
| 2012/0273550 A1 | 11/2012 | Scirica |
| 2012/0286019 A1 | 11/2012 | Hueil et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068820 A1 | 3/2013 | Miller et al. |
| 2013/0068821 A1 | 3/2013 | Huitema et al. |
| 2013/0075443 A1 | 3/2013 | Giordano |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |

(56) References Cited

U.S. PATENT DOCUMENTS

| | | |
|---|---|---|
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0119110 A1 | 5/2013 | Scirica |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |

FOREIGN PATENT DOCUMENTS

| | | |
|---|---|---|
| CA | 2773414 | 11/2012 |
| CN | 101006934 A | 8/2007 |
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 1 749 486 | 2/2007 |
| EP | 2090253 | 8/2009 |
| EP | 2090254 | 8/2009 |
| EP | 2583630 | 4/2013 |
| EP | 2586382 | 5/2013 |
| FR | 2681775 | 7/1983 |
| FR | 2542188 | 9/1984 |
| FR | 2660851 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| JP | 51-149985 | 6/1975 |
| JP | 2001-87272 | 4/2001 |
| SU | 659146 | 4/1979 |
| SU | 728848 | 5/1980 |
| SU | 980703 | 12/1982 |
| SU | 990220 | 1/1983 |
| WO | WO 8302247 | 7/1983 |
| WO | WO 89-10094 | 11/1989 |
| WO | WO 9210976 | 7/1992 |
| WO | WO 9308754 | 5/1993 |
| WO | WO 9314706 | 8/1993 |
| WO | WO 2004-032760 | 4/2004 |

OTHER PUBLICATIONS

Partial European Search Report dated Aug. 25, 2014 issued in EP 14 15 9080.
U.S. Appl. No. 14/159,012, filed Jan. 20, 2014, Hessler et al.
U.S. Appl. No. 14/230,516, filed Mar. 31, 2014, Cappola.
U.S. Appl. No. 14/270,853, filed May 6, 2014, Aranyi.
Chinese Office Action dated Apr. 12, 2017, issued in CH Application No. 201410093884X.

* cited by examiner

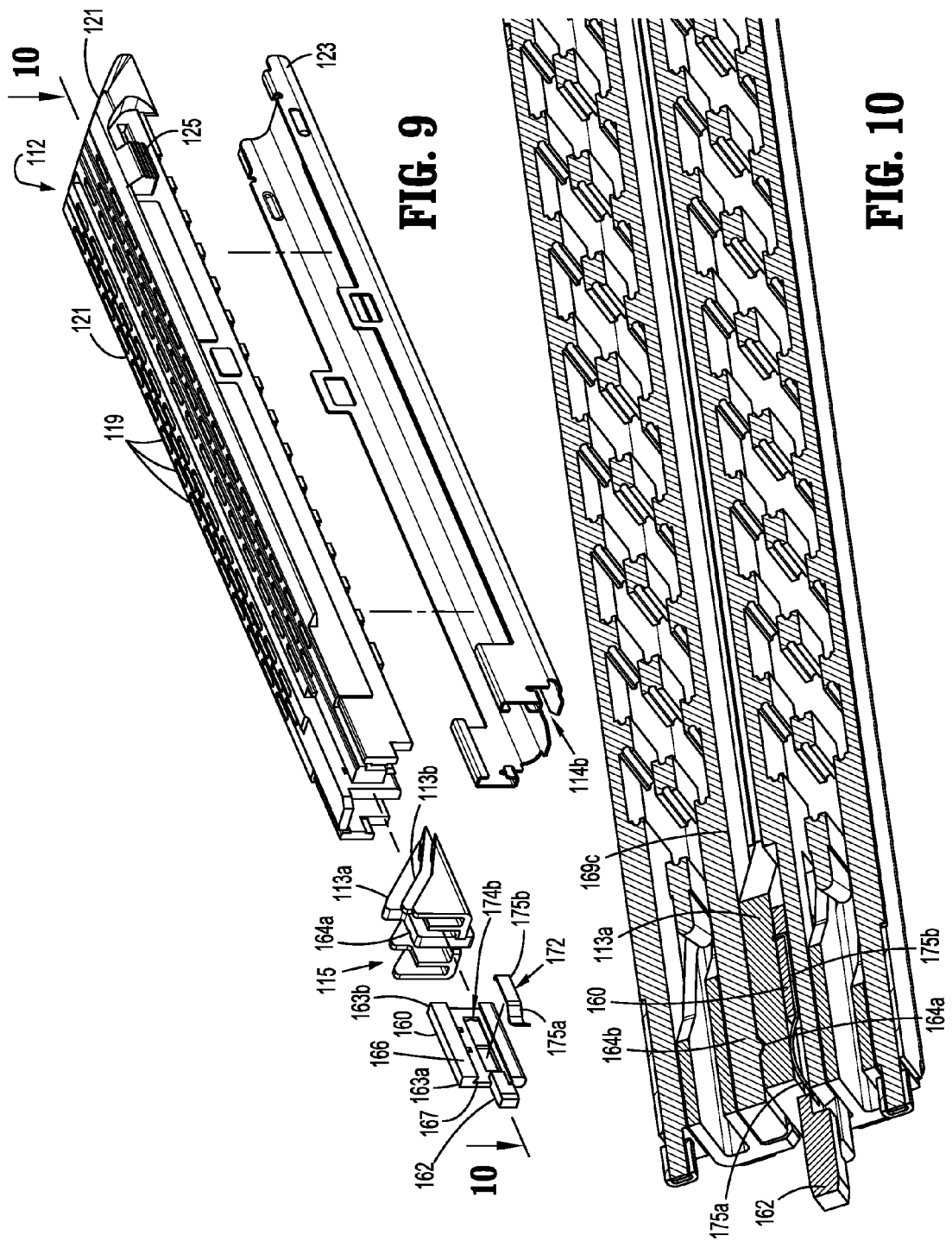

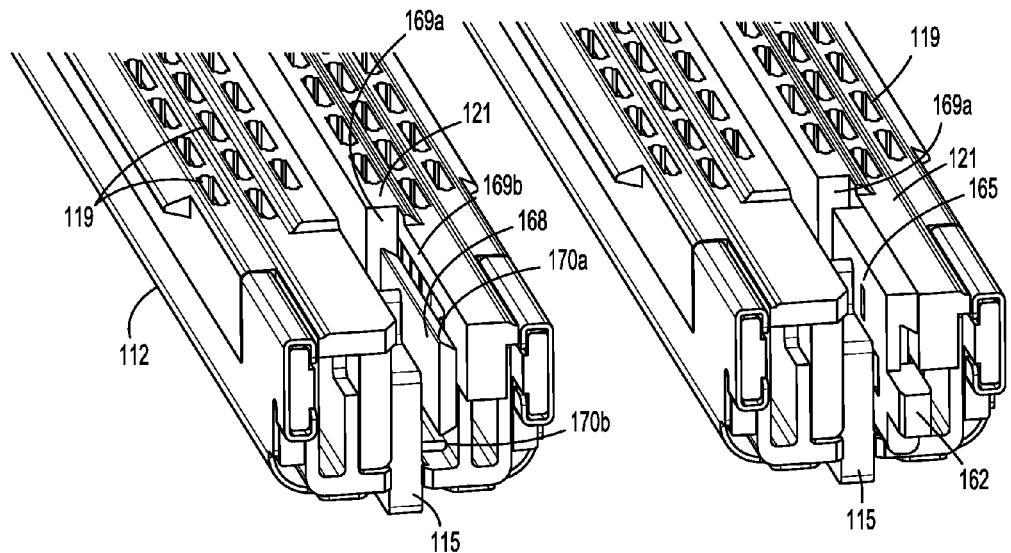
FIG. 11  FIG. 12
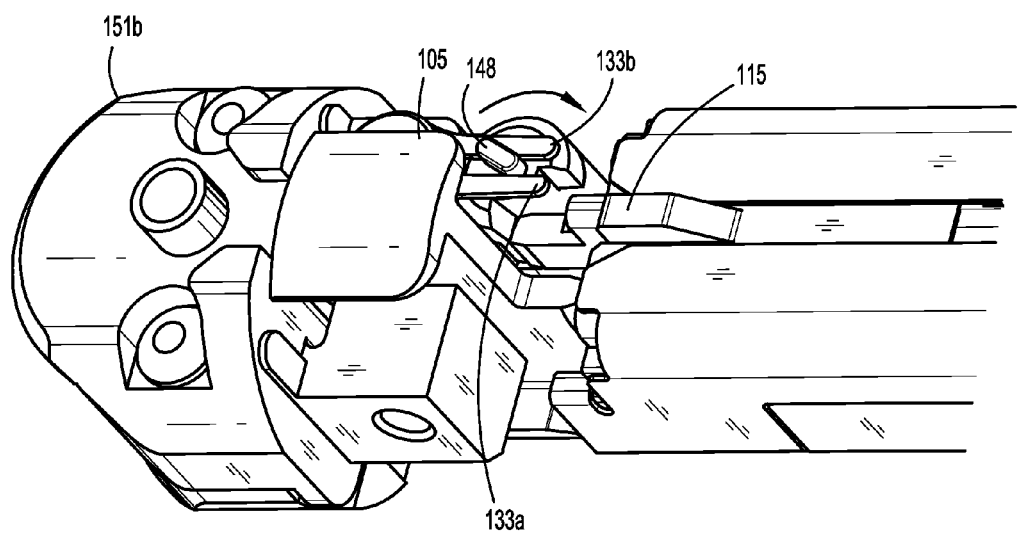
FIG. 13

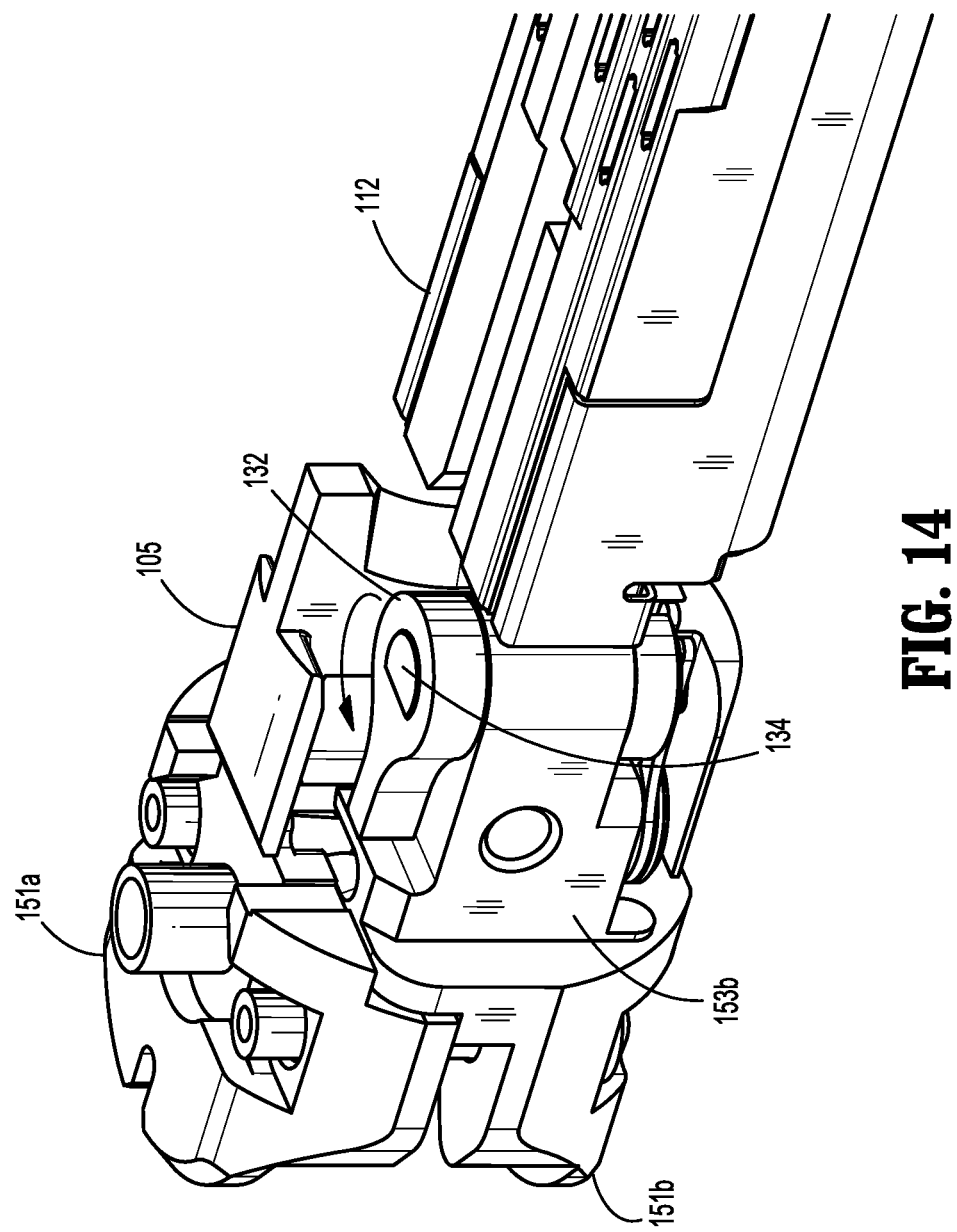

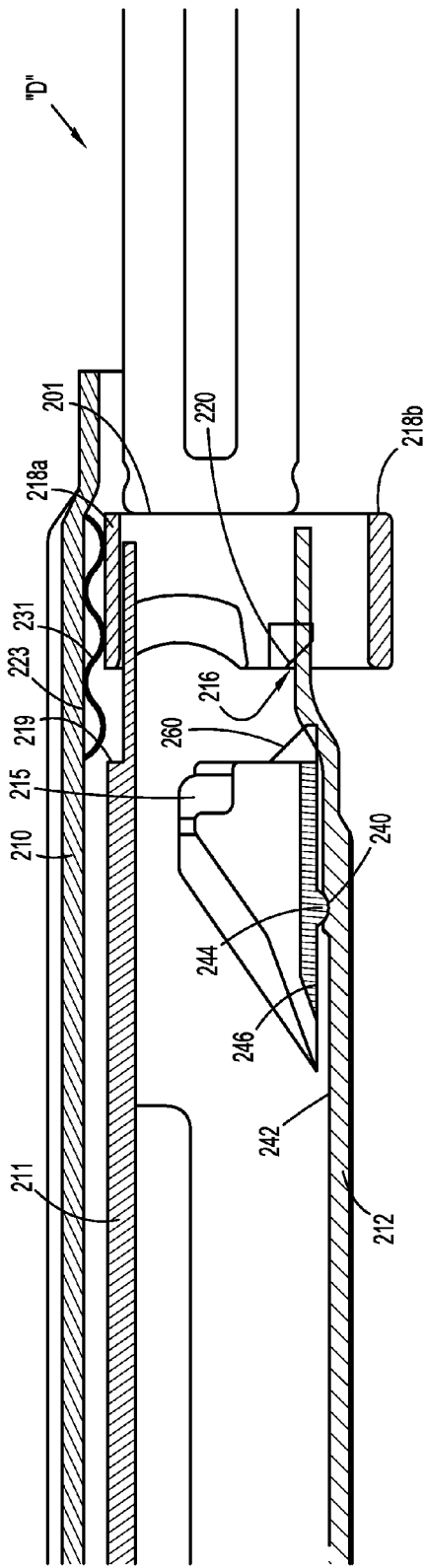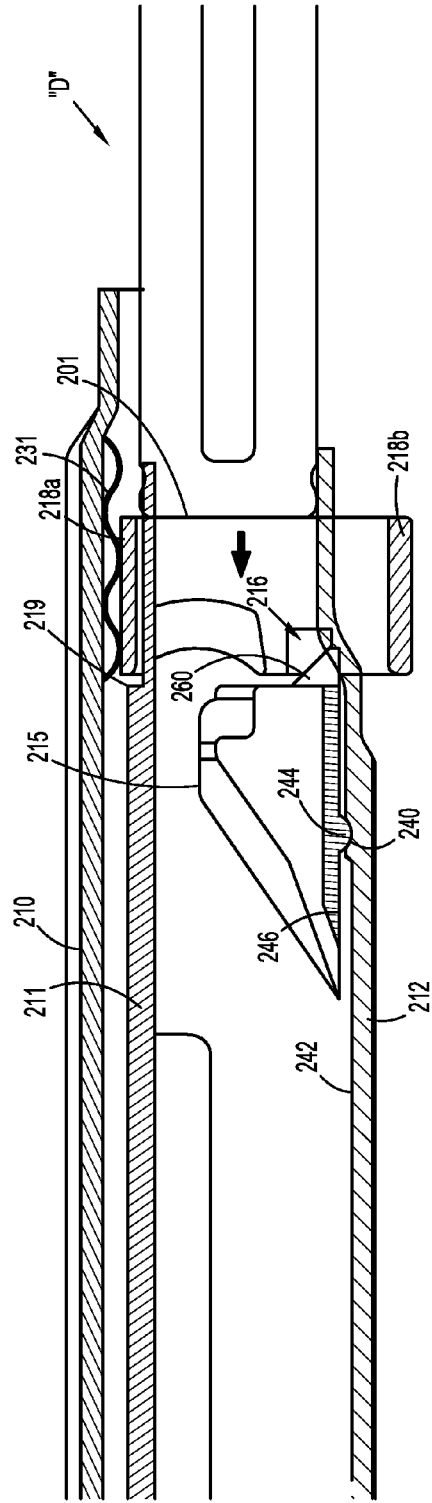

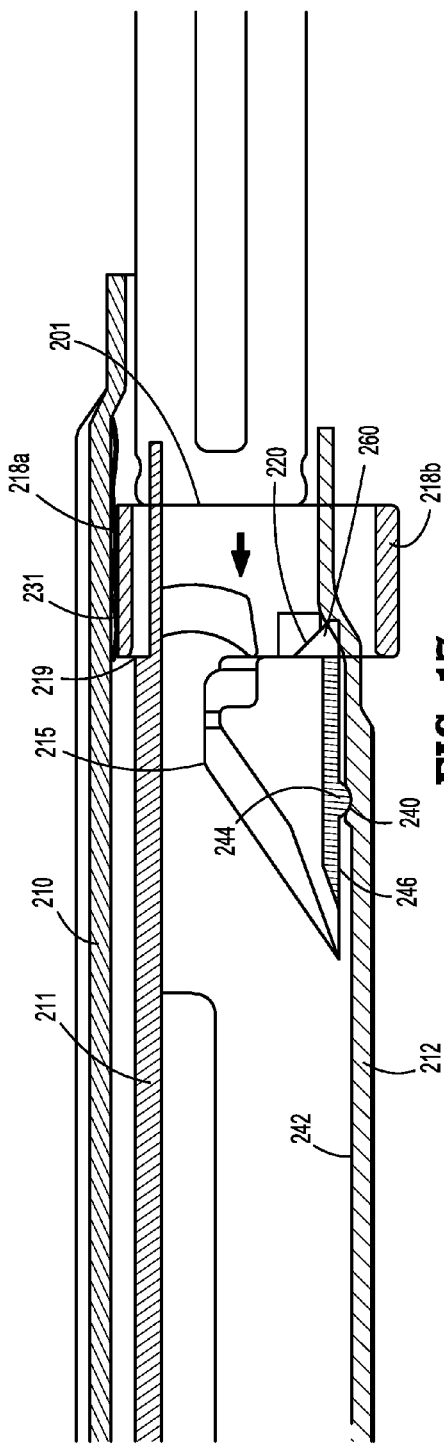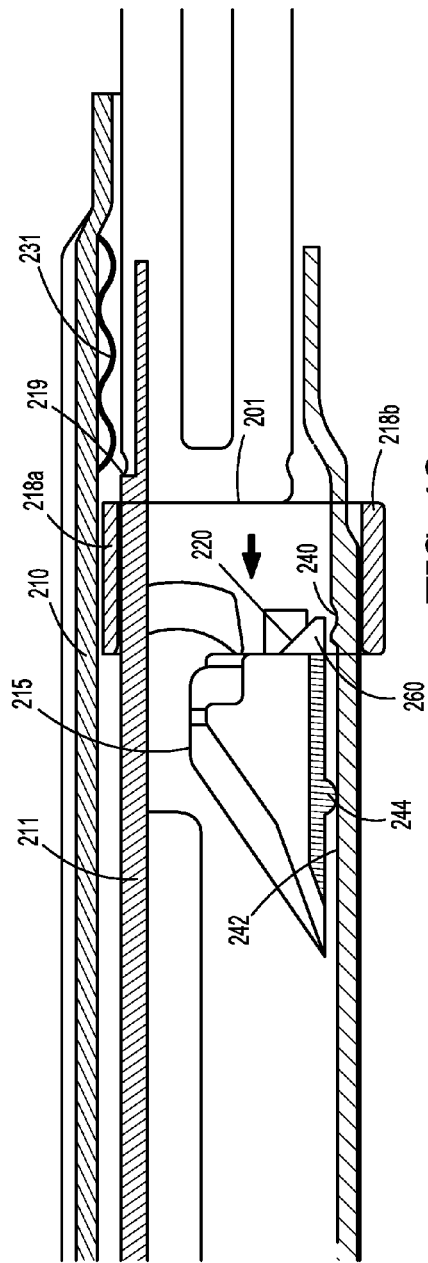
FIG. 17
FIG. 18

SURGICAL STAPLING APPARATUS

CROSS-REFERENCE TO RELATED APPLICATIONS

This application claims the benefit of and priority to U.S. Provisional Patent Application No. 61/779,631, filed Mar. 13, 2013, the entire disclosure of which is incorporated by reference herein.

BACKGROUND

Technical Field

The present disclosure relates to surgical stapling apparatuses. More particularly, the present disclosure relates to surgical stapling apparatuses including working end drive lockout mechanisms.

Description of Related Art

Surgical stapling apparatus configured to staple, and subsequently sever tissue are well known in the art. Such stapling apparatuses typically include a housing or handle and an elongated member that extends from the housing. In certain instances, single use or multi use loading unit (MULU) reload may be configured to releasably couple to a distal end of the elongated member. In either of the aforementioned reload configurations, a tool assembly including an anvil and a cartridge may be provided on respective jaws of the reload to staple tissue. The tool assembly can include a knife to sever the stapled tissue. The reload can include a drive member having a working end which supports the knife and advances an actuation sled through the tool assembly to staple and sever tissue.

While the aforementioned reload configurations provide numerous advantages, it may be desirable to prevent inadvertent advancement of the drive member of the reload when a staple cartridge is absent from the tool assembly or has been fired.

SUMMARY

As can be appreciated, surgical stapling apparatuses that include a drive lockout mechanism may prove useful in the surgical arena.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the instant disclosure provides a surgical stapling apparatus. The surgical stapling apparatus includes a housing and an elongated member therefrom. A tool assembly is supported on a distal end of the elongated member and includes a first jaw member and a second jaw member. A cartridge assembly is releasably supported on the first jaw member and includes an actuation sled and a slide. An anvil is operably supported on the second jaw member. A drive member having a working end is configured to translate through the tool assembly when the first and second jaw members are in a closed configuration. A lock assembly including a latch is movable from a locked position to an unlocked position. The latch is urged to the locked position to engage the working end of the drive member to prevent distal translation of the drive member through the tool assembly. The slide is configured to move the latch from the locked position to the unlocked position upon installation of an unspent cartridge assembly onto the first jaw member. The slide being movable by the drive member upon actuation of the stapling apparatus to allow the latch to move back to the locked position.

The lock assembly may be operably coupled to a pivot assembly of the reload. The lock assembly may include a cam pin, at least one resilient member and at least one washer. The cam pin may be positioned through an aperture defined through the pivot assembly and configured to rotate therein to move the latch from the locked position to the unlocked position when contacted by the slide.

The working end may include at least one recess that is configured to selectively engage the latch. The slide may be configured to releasably couple to the actuation sled. The slide may include at least one mechanical interface that is configured to couple to a corresponding mechanical interface disposed within the cartridge assembly when the actuation sled is moved distally. The mechanical interfaces may be disposed on the slide deflector and within the cartridge assembly form a dovetail joint.

An aspect of the instant disclosure provides a reload. The reload includes a tool assembly including a first jaw member and a second jaw member. A cartridge assembly is releasably supported on the first jaw member and includes an actuation sled and a slide. An anvil is operably supported on the second jaw member. A drive member having a working end is configured to translate through the tool assembly when the first and second jaw members are in a closed configuration. A lock assembly including a latch is movable from a locked position to an unlocked position. The latch is urged to the locked position to engage the working end of the drive member to prevent distal translation of the drive member through the tool assembly. The slide is configured to move the latch from the locked position to the unlocked position upon installation of an unspent cartridge assembly onto the first jaw member. The slide is movable by the drive member upon actuation of the stapling apparatus to allow the latch to move back to the locked position.

The lock assembly may be operably coupled to a pivot assembly of the reload. The lock assembly may include a cam pin, at least one resilient member and at least one washer. The cam pin may be positioned through an aperture defined through the pivot assembly and configured to rotate therein to move the latch from the locked position to the unlocked position when contacted by the slide.

The working end may include at least one recess that is configured to selectively engage the latch. The slide may be configured to releasably couple to the actuation sled. The slide may include at least one mechanical interface that is configured to couple to a corresponding mechanical interface disposed within the cartridge assembly when the actuation sled is moved distally. The mechanical interfaces may be disposed on the slide deflector and within the cartridge assembly form a dovetail joint.

An aspect of the instant disclosure provides a surgical stapling apparatus. The surgical stapling apparatus includes a housing and an elongated member therefrom. A tool assembly is supported on a distal end of the elongated member and includes a first jaw member and a second jaw member. A cartridge assembly is releasably supported on the first jaw member and includes an actuation sled including at least one mechanical interface. An anvil is operably supported on the second jaw member and includes at least one spring and defines a stop. A drive member having a working end includes at least one mechanical interface. The spring is configured to urge the working end of the drive member to position the working end of the drive member in alignment with the stop on the anvil to prevent the working end of the drive member being advanced distally. The at least one mechanical interface on the actuation sled is positioned to engage the at least one mechanical interface on the working end of the drive member to retain the working end of the drive member out of engagement with the stop to allow advancement of the drive member through the tool assembly.

The at least one mechanical interface on the actuation sled may be a protuberance having a slanted configuration that extends proximally and the at least one mechanical interface on the working end is a recess having a configuration that complements the slanted configuration of the protuberance. The actuation sled may include a detent that may be configured to releasably engage a corresponding indent disposed within the cartridge assembly.

The spring may be configured to contact a top portion of the working end of the drive member for biasing the working end in the generally downward direction. The wave spring may be a wave spring.

An aspect of the instant disclosure provides a reload. The reload includes a tool assembly including a first jaw member and a second jaw member. A cartridge assembly is releasably supported on the first jaw member and includes an actuation sled including at least one mechanical interface. An anvil is operably supported on the second jaw member and includes at least one spring and defines a stop. A drive member having a working end includes at least one mechanical interface. The spring is configured to urge the working end of the drive member to position the working end of the drive member in alignment with the stop on the anvil to prevent the working end of the drive member being advanced distally. The at least one mechanical interface on the actuation sled is positioned to engage the at least one mechanical interface on the working end of the drive member to retain the working end of the drive member out of engagement with the stop to allow advancement of the drive member through the tool assembly.

BRIEF DESCRIPTION OF THE DRAWING

Various embodiments of the present disclosure are described hereinbelow with references to the drawings, wherein:

FIG. 9 perspective view of the cartridge assembly and jaw shown in FIG. 3B separated from one another and with an actuation and slide of the cartridge assembly separated from the cartridge assembly;

FIG. 10 is a cross-sectional view taken along line portion 10 in FIG. 9;

FIG. 11 is a partial, perspective view of a proximal end of the cartridge assembly with the slide removed to show a guide of the cartridge assembly;

FIG. 12 is a partial, perspective view of the proximal end of the cartridge assembly with the slide shown coupled to the guide provided shown in FIG. 11;

FIG. 13 is a partial, perspective view of the proximal end of the tool assembly shown in FIG. 3B illustrating a top portion of the pivot assembly shown in FIG. 4 with the cartridge assembly installed on the jaw member and the working end of the reload is in a pre-advanced position;

FIG. 14 is a partial, perspective view of the proximal end of the tool assembly shown in FIG. 3B illustrating a bottom portion of the pivot assembly shown in FIG. 4 with the cartridge assembly installed on the jaw member and the working end of the reload in a pre-advanced position;

FIG. 15 is a side, cross-sectional view of a tool assembly of a reload including a drive lockout mechanism according to an alternate embodiment of the instant disclosure and with a working end in a retracted position;

FIG. 16 is a partial, cross-sectional view of the tool assembly with the working end of the reload being advanced distally towards an actuation sled of a cartridge assembly of the reload;

FIG. 17 is a partial, cross-sectional view of the tool assembly with the working end of the reload engaged with the actuation sled and with the working end positioned for further advancement thereof through the reload;

FIG. 18 is a partial, cross-sectional view of the tool assembly with the working end engaged with the actuation sled and being translated through cartridge assembly.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with the instant disclosure, various drive lockout mechanisms are disclosed herein and are configured for use with surgical stapling apparatus adapted to receive replaceable staple cartridge. The various drive lockout mechanisms described below are configured to prevent firing of the surgical stapling apparatus prior to installing a cartridge, or including a spent or empty cartridge installed.

Figure 1:
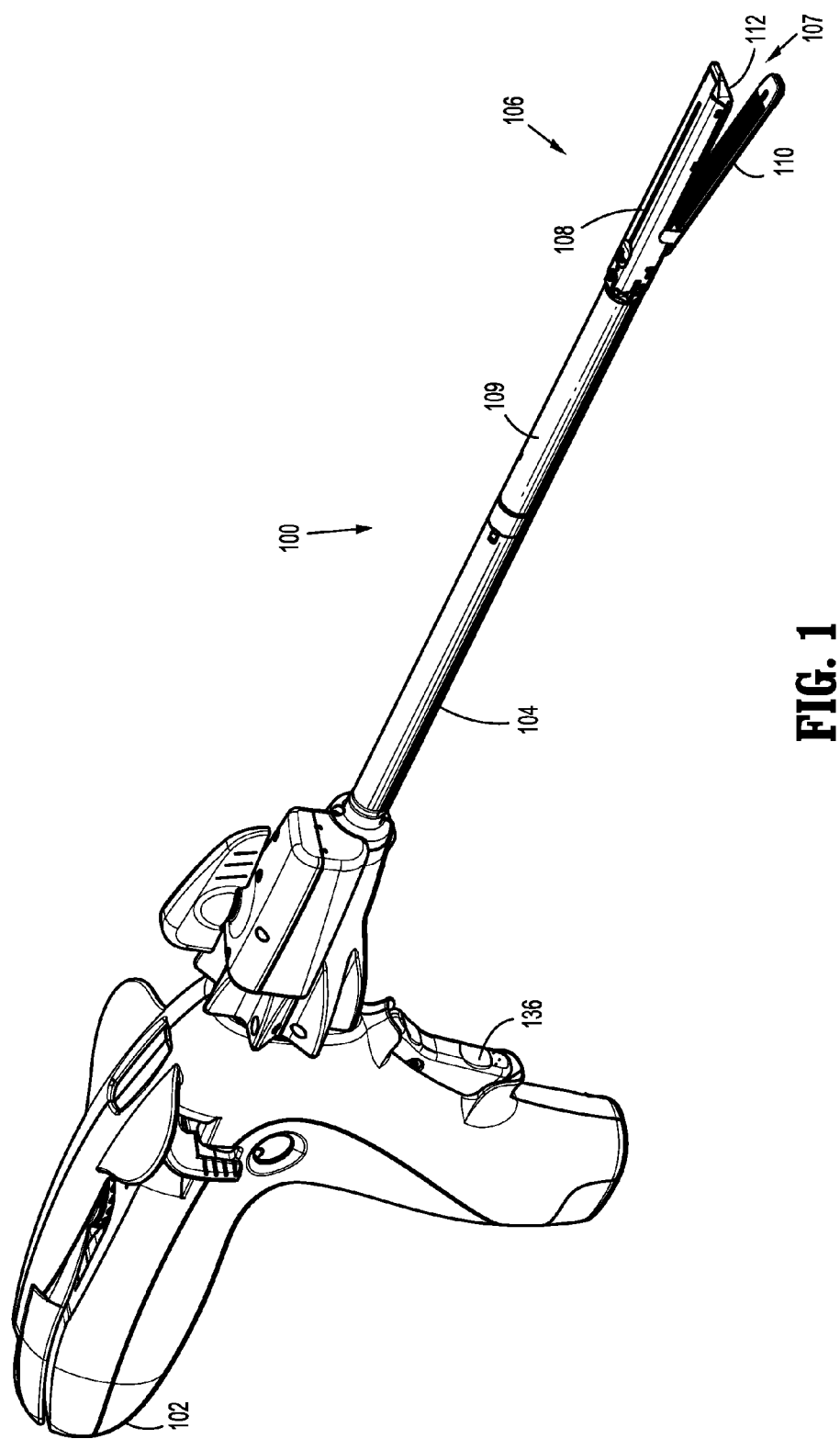
FIG. 1 is a side, perspective view of a powered surgical stapling apparatus supporting a reload.
Figure 2:
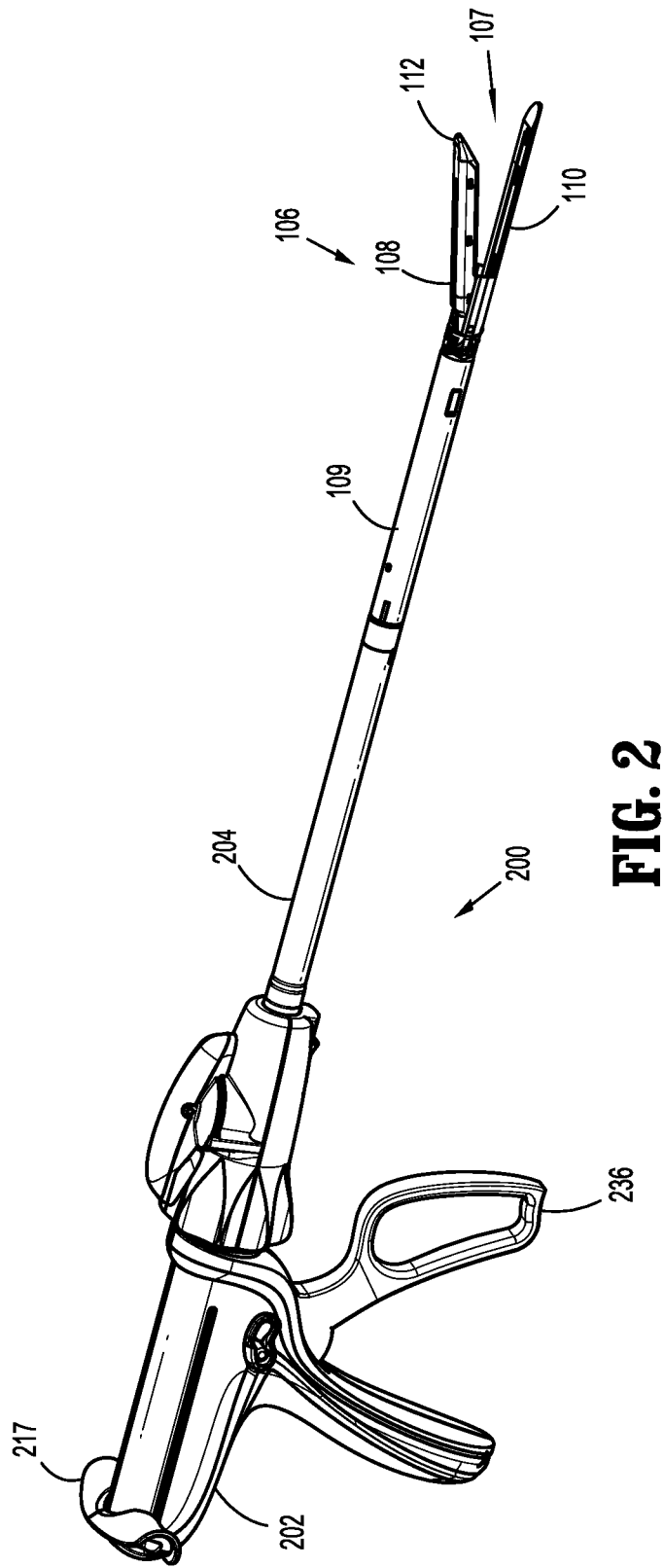
FIG. 2 is a side, perspective view of a manual surgical stapling apparatus supporting a reload.

FIG. 1 illustrates a powered surgical stapling apparatus shown generally as 100. FIG. 2 illustrates a manual surgical stapling apparatus shown generally as 200. The powered apparatus includes one or more motors and an internal or external power source for mechanically actuating the stapling apparatus, whereas the manual apparatus 200 has a movable handle 236 for manually actuating the stapling apparatus. See U.S. Pat. Nos. 5,865,361; 5,782,396; International WO 04/032,760; U.S. Patent Publication No. 2010/

0276741; and U.S. patent application Ser. No. 13/444,228, the entire contents of each of these disclosures is hereby incorporated herein by reference.

Briefly, the surgical stapling apparatus 100 includes a housing or stationary handle 102 having an actuator 136 and an elongated member 104 extending from housing 102 (FIG. 1). Likewise, surgical stapling apparatus 200 includes a housing or stationary handle 202 supporting a movable handle 236 and an elongated member 204 extending from housing 202. Surgical stapling apparatus 200 includes a retraction mechanism 217 (FIG. 2) that can be manually grasped and pulled proximally to retract a firing mechanism of the apparatus 200. Each of elongated members 104, 204 is configured to removably couple to a reload 106. Although the embodiments described herein disclose a reload 106 including a tool assembly 107 which is releasably coupled to the elongate member 104, 204, it is envisioned that the tool assembly can be fixedly secured to the distal end of the elongated member 104, 204.

Figure 3A:
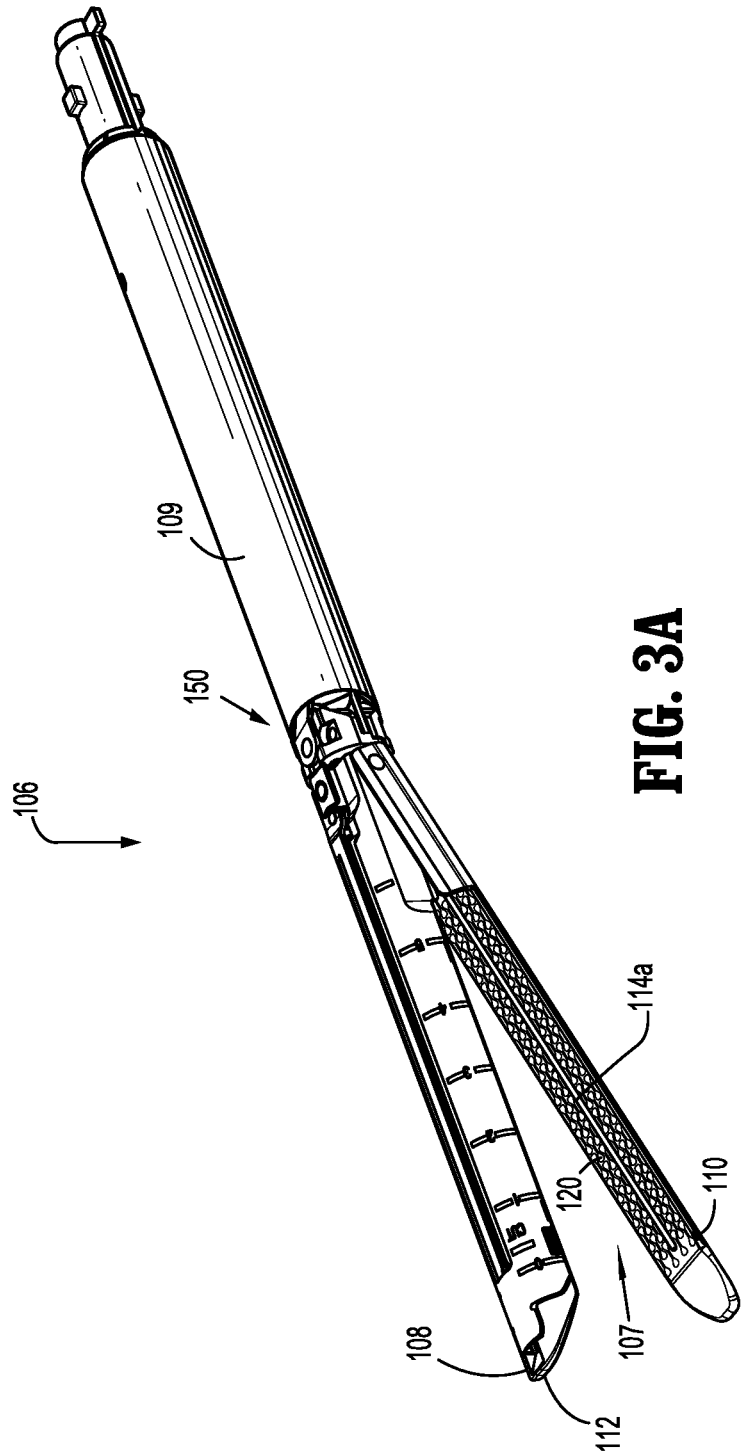
FIG. 3A is a side perspective view of the reload of FIGS. 1 and 2 including a drive lockout mechanism according to an embodiment of the instant disclosure.

Referring to FIG. 3A, the reload 106 includes a shaft portion 109 and a tool assembly 107 supported on a distal end of the shaft portion 109. The tool assembly 107 includes first and second jaw members 108, 110 which are movable from a spaced apart configuration (FIG. 2) for positioning tissue therebetween to an approximated configuration (not shown) for clamping tissue and subsequently stapling tissue. Jaw member 108 releasably supports a cartridge assembly 112 and jaw member 110 supports an anvil 111 that includes a plurality of buckets or depressions 120 that are configured to receive corresponding fasteners (not shown) when the fasteners are deployed from the cartridge 112.

Reference may be made to U.S. Pat. Nos. 5,865,361 and 7,225,963, the entire contents of which are incorporated herein by reference, for a more detailed discussion of the construction and operation of reload 106.

Figure 3B:
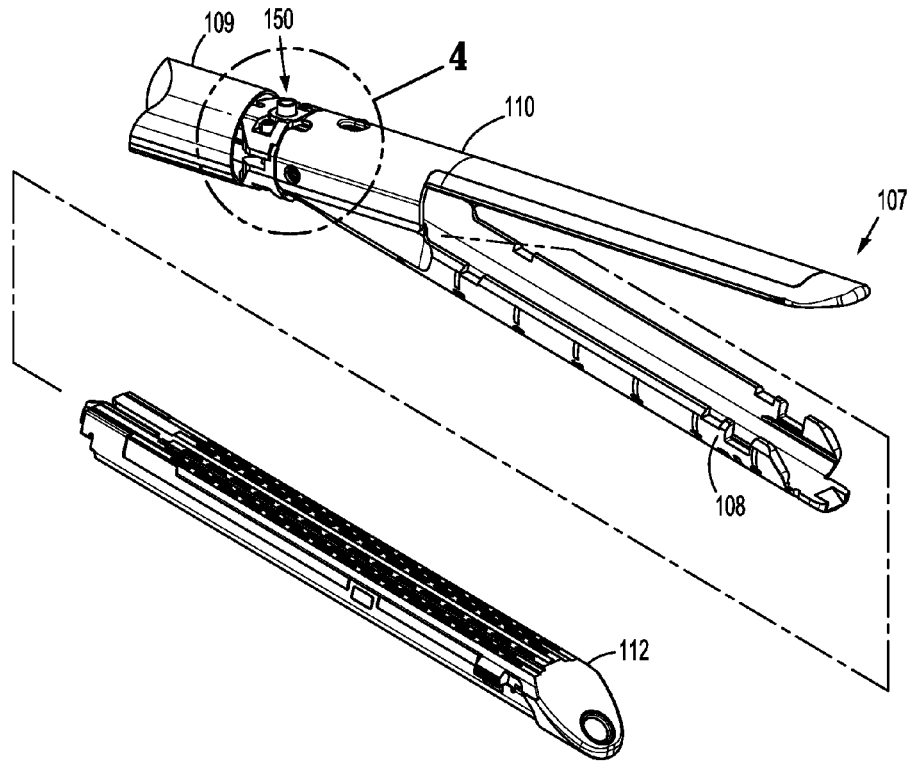
FIG. 3B is a side, perspective view of a tool assembly of the reload shown in FIGS. 1-3A.

FIG. 3B illustrates the tool assembly 107 of the reload with the jaw members 108, 110 in an approximated configuration and with cartridge 112 separated from the jaw member 108. The reload 106 includes a locking mechanism that is configured to lock-out a drive member "D" (FIG. 5) so as to prevent firing of the apparatus when a cartridge 112 has not been installed in the jaw member 108 or when the cartridge 112 installed in jaw member 108 has already been fired.

Figure 4:
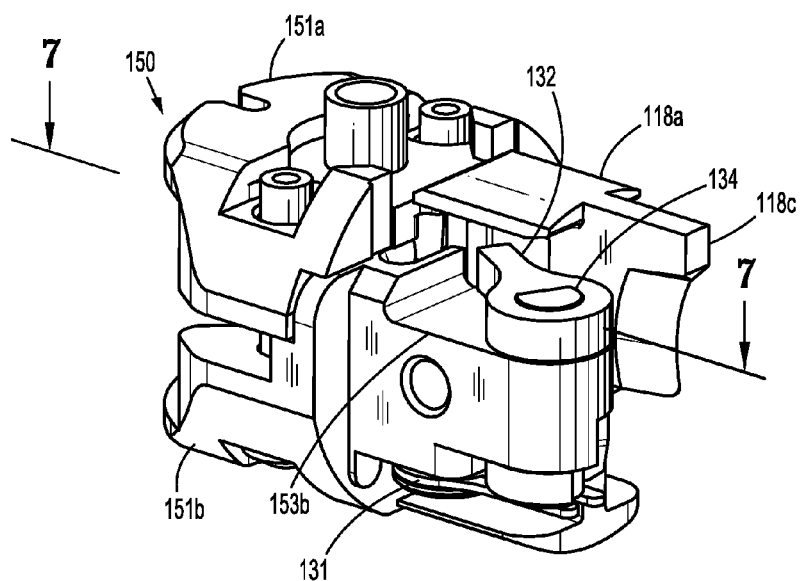
FIG. 4 is an enlarged view of the indicated area of detail of FIG. 3C.
Figures 5, 6:
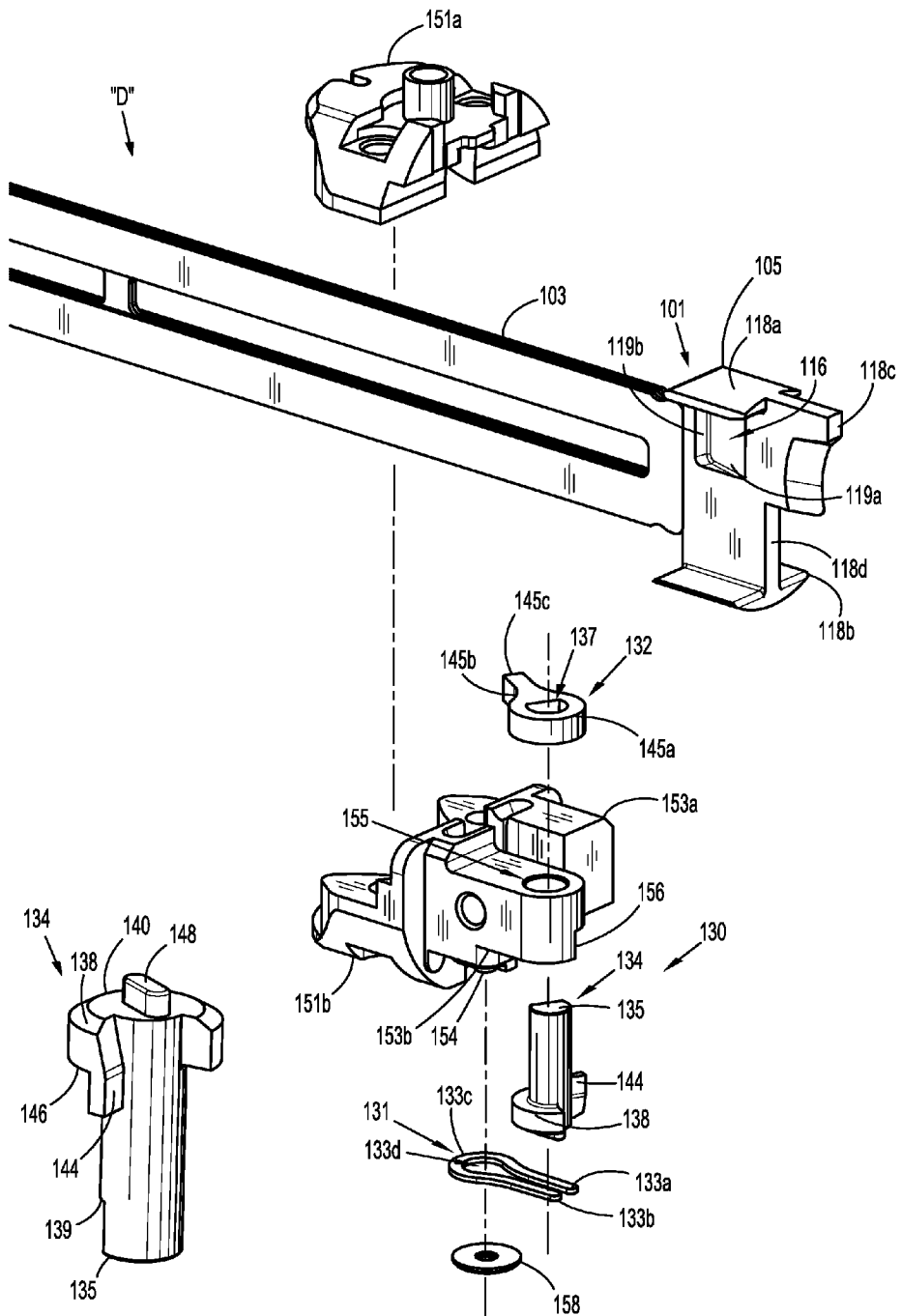
FIG. 5 is an exploded view of the pivot assembly shown in FIG. 4 and a drive member including a working end of the reload shown separated from one another.
FIG. 6 is a perspective view of the cam pin shown in FIG. 5.

A pivot assembly 150 (FIG. 3B) is provided at a distal end of shaft 109 which pivotally couples tool assembly 107 to shaft 109. Referring to FIGS. 4-5, pivot assembly 150 includes top and bottom portions 151a, 151b that are operably coupled to one another and to jaw members 108, 110, respectively, so as to allow articulation of jaw members 108, 110 (FIG. 3B) about an axis transverse to the longitudinal axis of the reload 106. Bottom portion 151b of pivot assembly 150 is configured to operably support a lock assembly 130 that is operable to prevent advancement of the working end 101 of drive member "D" distally when the cartridge 112 has been fired or is absent from the jaw member 108. Specifically, bottom portion 151b includes a pair of distally extending leg members 153a, 153b. Leg members 153a, 153b are spaced-apart from one another to receive a drive beam 103 of drive member "D" therebetween (FIGS. 4-5 and 7-8) so as to allow advancement of working end 101 though the cartridge 112, as will be described in greater detail below. Leg members 153a, 153b include a generally elongated configuration. In the illustrated embodiment, leg member 153b is slightly longer than leg member 153a and includes a distal end having a generally arcuate configuration. While leg member 153b is illustrated having a length that is greater than a length of leg member 153a, it is within the purview of the present disclosure to provide leg members 153a, 153b with the same length.

An aperture 155 extends through a distal end of leg member 153b to receive a cam pin 134 of lock assembly 130. A notch 156 is provided on leg member 153b adjacent aperture 155 and is positioned to receive a cam feature 144 of cam pin 134 to allow rotation of the cam pin 134 within aperture 155, as will be described in greater detail below.

Referring to FIGS. 4-8, lock assembly 130 includes a latch 132, cam pin 134 and a spring clip 131. Cam pin 134 is configured to rotate within aperture 155 as cartridge 112 is being installed on jaw member 108 in response to engagement with slide 160. To this end, cam pin 134 includes a generally elongated configuration including an upper portion 135 having a non circular configuration that is configured to be non-rotatably received within a corresponding aperture 137 that is defined through latch 132. As such, rotation of cam pin 134 causes corresponding rotation of latch 132 between locked (FIG. 7) and unlocked positions. A shelf 139 (FIG. 6) is provided on cam pin 134 adjacent top portion 135 and aligns with a top, planar surface of leg member 153b when cam pin 134 is seated within aperture 155. In embodiments, for example, shelf 139 may be utilized to help support latch 132 and/or raise latch 132 off of the top surface of leg member 153b.

Cam pin 134 includes a base 140 having a flange portion 138 that engages a bottom portion of leg member 153b adjacent notched portion 156 when cam pin 134 is seated within aperture 155 of leg member 153b. Flange portion 138 is provided adjacent base 140 and extends partially along an outer circumferential surface of cam pin 134. Flange 138 includes a cam feature 144 that is configured to engage a cam extension 162 disposed on a slide 160 (FIG. 9) that is releasably coupled to an actuation sled 115 of cartridge 112 when cartridge 112 is being installed on jaw member 108, as will be described in greater detail below.

Figure 7:
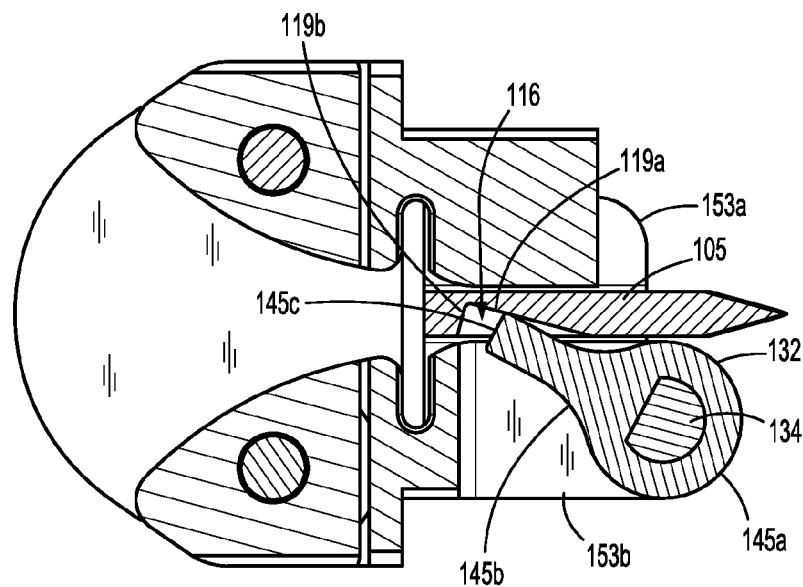
FIG. 7 is a partial, cross-sectional view taken along line portion 7 in FIG. 4.
Figure 8:
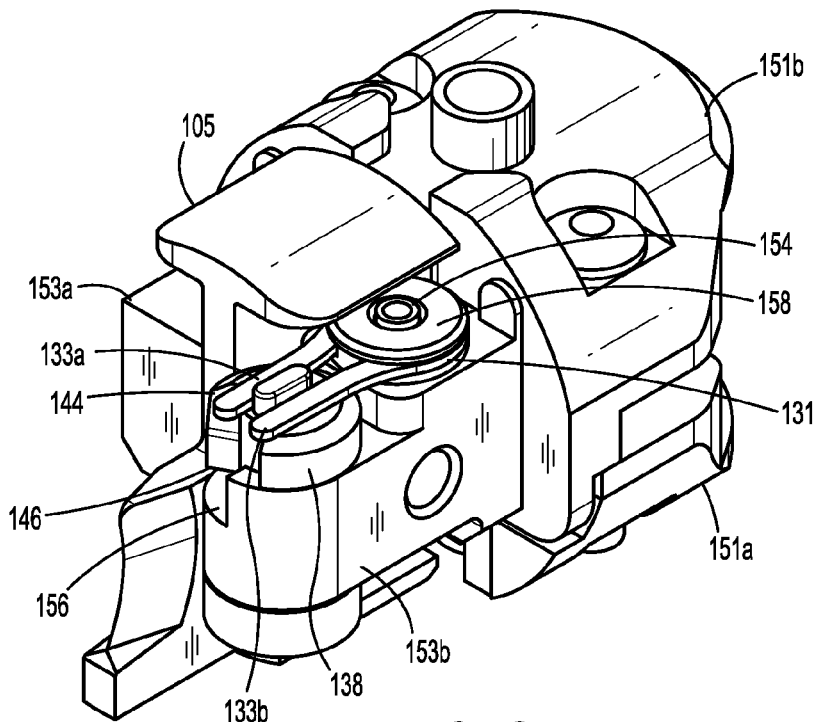
FIG. 8 is a side, perspective view of the pivot assembly depicted in FIG. 4 shown inverted.
Figure 19:
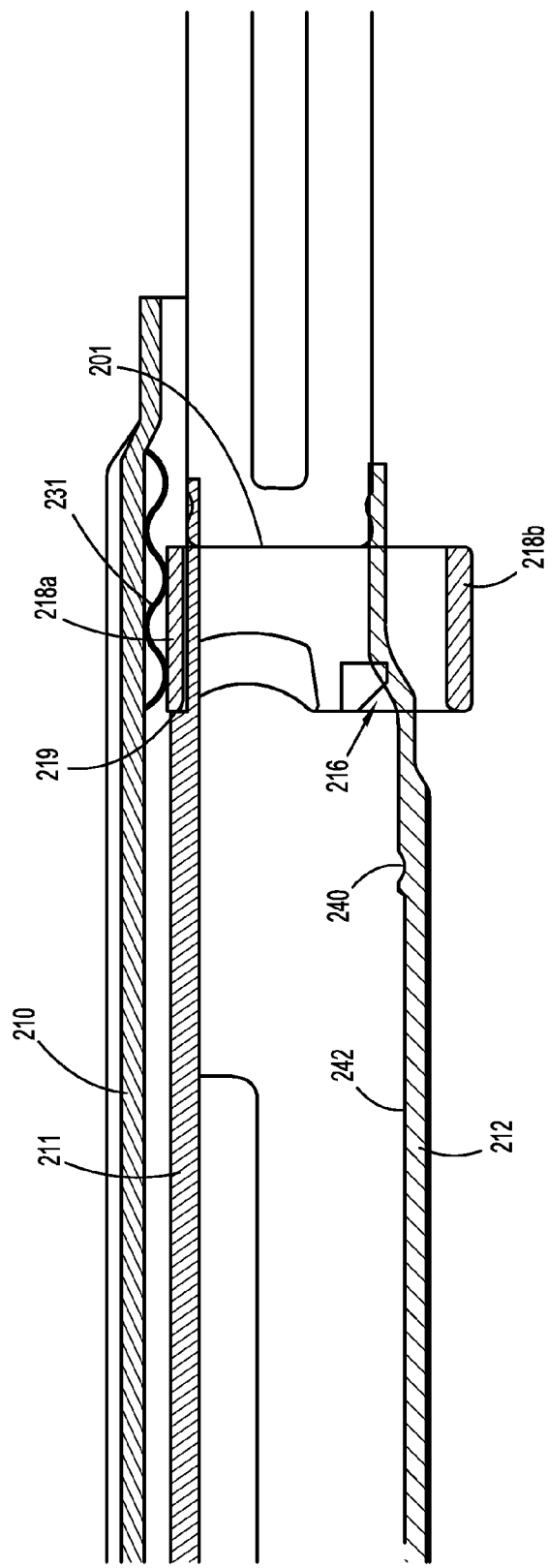
FIG. 19 is a partial, cross-sectional view of the tool assembly with the working end in the retracted position.

A top surface 146 of flange portion 138 is generally planar and is positioned to abut a bottom surface of leg member 153b such that cam feature 144 is disposed within notch 156 of leg member 133b when cam pin 134 is positioned through aperture 155 (as best seen in FIG. 8). Cam feature 144 is movable within the recess 156 as to allow rotation of cam pin 134 within aperture 155 when cartridge 112 is being installed and when working end 101 of drive member "D" is returned to the retracted position. Cam pin 134 is rotatable within aperture 155 from a position in which latch 132 obstructs movement of the drive member "D" (FIG. 7) to a position in which latch 132 is spaced from drive member "D," as will be discussed in further detail below.

A protrusion 148 is provided on base 140 of cam pin 134 and is received between spaced-apart resilient leg portions 133a, 133b of spring clip 131 (as best seen in FIG. 8). Protrusion 148 is positioned between the leg portions 133a, 133b such that rotation of cam pin 134 within aperture 155 causes resilient leg portions 133a, 133b deflect outwardly (FIG. 13). Leg portions 133a, 133b are configured to contact protrusion 148 to retain cam pin 134 and, thus, latch 132 in the locked position, as shown in FIG. 7. In the locked position, latch 132 is positioned to engage a recess 116 provided on working end 101 of drive member "D" (FIG. 5) to prevent distal advancement of drive member "D." In the locked position, protrusion 148 extends parallel to and between leg portions 133a, 133b (FIG. 8) and the leg portions 133a, 133b are unbiased. When cartridge 112 is installed in jaw member 108, cam extension 162 of slide 160 contacts cam feature 144 and moves cam feature 144 proximally, which, in turn, rotates cam pin 134 and, thus, rotates protrusion 148 into contact with leg portions 133a, 133b (FIG. 13) to deflect leg portions 133a, 133b of spring clip 131 outwardly. As a result thereof, latch 132 is rotated out of engagement with recess 116 of working end 101 to facilitate distal advancement of the drive member "D." Cam extension 162 of slide 160 remains engaged with cam feature 144 of cam pin 134 until such time that working end 101 is advanced and caused to engage actuation sled 115. When this occurs, movement of cam extension 162 out of engagement with cam feature 144 allows protrusion 148 to return to the locked out configuration as a result of the biasing force provided by leg portions 133a, 133b of spring clip 131 on protrusion 148.

Leg portions 133a, 133b of spring clip 131 meet at a generally arcuate proximal end 133c of spring clip 131 (FIG. 5). The arcuate configuration of proximal end 133c provides a suitable spring constant that allows leg portions 133a, 133b to bias the protrusion 148 such that the latch 132 is moved to the locked position when slide 160 is disengaged from cam feature 144 of cam pin 134.

An aperture 133d of spring clip 131 is provided adjacent proximal end 133c and is configured to receive a corresponding rivet 154 (or other suitable device) that is provided on a bottom portion 151b of pivot assembly 150 (FIGS. 5 and 8). A washer 158 may be utilized to couple to rivet 154 for securing lock assembly 130 to bottom portion 151b.

Latch 132 is configured to prevent distal advancement of working end 101 of drive member "D" when the latch 132 is in a locked position. Latch 132 includes an end 145a that defines the aperture 137. A generally elongated member 145b extends from end 145a and includes a tip 145c that is configured to be releasably received within recess 116 (FIG. 7) of working end 101 of the drive member "D."

With reference again to FIG. 5, drive member "D" includes a drive beam 103 which supports the working end 101. Working end 101 has an I-beam configuration having top and bottom flanges 118a, 118b and includes a distal abutment surface 118c which engages a central support wedge 113a (FIG. 9) of the actuation sled 115 (FIG. 9). Working end 101 is configured to move through the tool assembly 107 which includes knife channel portions 114a (FIG. 3A), 114b (FIG. 9) that are defined through an anvil 111 which is supported on the jaw member 110 and jaw member 108, respectively. Specifically, the working end 101 of the drive beam 103 moves from a retracted position to an extended position to advance the working end 101 and the actuation sled 115 through a cartridge 112 to staple and sever tissue. The knife 105 is positioned to travel slightly behind the actuation sled 115 during a stapling procedure to form an incision between the rows of stapled tissue.

The recess 116 is provided at a proximal end of working end 101 of drive member "D" adjacent top flange 118a and is defined by a sidewall 119a and a back wall 119b. Sidewall 119a is angled and extends distally from back wall 119b. The recess 116 is configured to slidably receive distal tip 145c of elongated member 145b and guide distal tip 145c towards back wall 119b to lock out working end 101, as best seen in FIG. 7.

In accordance with the instant disclosure, prior to installing cartridge 112 onto jaw member 108, working end 101 of drive member "D" is retracted and in the locked out position. More specifically, leg portions 133a, 133b of spring clip 131 are positioned to retain protrusion 148 of cam pin 134 at an orientation to position latch 132 in the locked put position (FIG. 7). In order to move the latch 132 from the locked position, an unfired cartridge 112 must be installed on jaw member 108 as discussed below.

With reference to FIGS. 9-14, jaw member 108 of tool assembly 107 is configured to support removable cartridge assembly 112 thereon. Cartridge 112 includes the plurality of fasteners and a plurality of pusher members (not shown) that are operatively engaged with the fasteners. Cartridge 112 also includes one or more retention slots 119 that are positioned longitudinally along a tissue contacting surface 121 of cartridge 112 and are configured to house a plurality of fasteners (not shown). A cartridge housing 123 (FIG. 9) is coupled to jaw member 108. In any of the embodiments disclosed herein, cartridge 112 may be coupled to jaw 108 using detents 125 (FIG. 9), latches, clips or the like. A removable and replaceable cartridge is disclosed in U.S. patent application Ser. No. 13/280,880 entitled Multi-Use Loading Unit, the entire disclosure of which is hereby incorporated by reference herein.

An actuation sled 115 is positioned at a proximal end of cartridge 112 and is held in place within cartridge 112 via an indent/detent configuration. Specifically, an indent 164a is provided on a side surface 165 of a central wedge support 113a and engages a corresponding detent 164b that is provided on a left interior side wall 149c of cartridge 112 (FIG. 10). Detent 164b is configured to release from indent 164a when working end 101 of drive member "D" contacts actuation sled 115 and is advanced distally through cartridge 112.

Slide 160 has a generally elongated configuration with proximal and distal ends 163a, 163b. The cam extension 162 (a generally elongated protrusion, detent or the like) is provided at the proximal end 163a of slide 160 and is positioned on actuation sled 115 to engage the cam feature 144 of lockout assembly 130 to rotate latch 132 into the unlocked position when cartridge 112 is being coupled to jaw member 108 (FIGS. 12-13).

Slide 160 is supported between raised wedge supports of the actuation sled 115 to releasably couple the slide 160 to the actuation sled 115. Specifically, slide 160 is coupled to actuation sled 115 between the central wedge support 113a and a right wedge support 113b of actuation sled 115 (FIG. 9). More specifically, slide 160 releasably couples to actuation sled 115 via a resilient member in the form of a spring 172 (band, coil or the like) having proximal and distal ends 175a, 175b. Proximal end 175a of spring 172 is configured to bias proximal end 163a of the slide 160 against a proximal end of the right support wedge 113b such that slide 160 remains coupled to actuation sled 115 as cartridge 112 is being installed onto jaw member 108 and cam extension 162 engages cam feature 144 to move latch 132 out of engagement with recess 116 of working end 101 of the drive member "D." Spring 172 may also be utilized to facilitate biasing detent 164b of cartridge 112 into engagement with indent 164a of actuation sled 115. Spring 172 is press or friction fit into a pair of corresponding recesses 174a, 174b that are provided on a sidewall 166. Specifically, recess 174b is disposed distal of recess 174a and is configured to receive the distal end 175b of spring 172. The proximal end 175a of spring 172 is received within recess 174a.

Sidewall 166 of slide 160 defines a groove 167 configured to receive a corresponding guide member 168 which extends from a right interior sidewall 169b of cartridge 112 (FIG. 11). Right interior sidewall 169b including guide member 168 is positioned within cartridge 112 to allow distal translation of actuation sled 115 through cartridge 112. In one embodiment, groove 167 has a dovetail configuration and receives the guide member 168 of corresponding shape.

Referring to FIGS. 11-12, in accordance with the instant disclosure, when working end 101 of drive member "D" is advanced to contact and advance the actuation sled 115, working end 101 and actuation sled 115 including slide 160 initially move distally in unison (spring 172 maintains slide 160 and actuation sled coupled to one another). Continued distal translation of the working end 101 of the drive member "D" causes groove 167 to receive guide member 168. Guide member 168 guides slide 160 into engagement with an interior wall 169a of cartridge 112 (FIGS. 11-12) adjacent right interior sidewall 169b to prevent further distal movement of the slide 160. When distal end 163b of the slide 160 contacts interior wall 169a, slide 160 disengages from actuation sled 115. With groove 167 engaged with guide member 168, slide 160 is secured to interior sidewall 169b and prevented from further movement within cartridge 112. As such, when working end 101 of drive member "D" is moved back to the retracted configuration, the slide 160 is retained in the advanced position with the distal end 163b in contact with interior wall 169a.

In use, when a cartridge assembly 112 is not installed on jaw member 108, latch 132 is in a locked configuration with distal tip 145c of latch 132 positioned within recess 116 of working end 101 (FIG. 7). With distal tip 145c of latch 132 in this configuration, as the drive member "D" is advanced distally, engagement between distal tip 145c and back wall 119b of recess 116 prevents further advancement of drive member "D" (drive member "D" is locked out) (FIGS. 7-8).

When the cartridge 112 is installed in jaw member 108, cam extension 162 of slide 160 contacts cam feature 144 of cam pin 134 to rotate cam pin 134 within aperture 155. Rotation of cam pin 134 effects corresponding rotation of latch 132 to move latch 132 out of engagement with recess 116 of working end 101. In this position, protrusion 148 of cam pin 134 deflects leg portions 133a, 133b of spring clip 131 outwardly such that leg portions 133a, 133b of spring clip 131 urge cam pin 134 back to a position in which the latch 132 is in the locked position as described above, see FIGS. 13-14 for example. Moreover, slide 160 is maintained coupled to actuation sled 115 in a manner as described above.

With latch 132 and slide 160 in the pre-fired configuration, drive member "D" including working end 101 is allowed to translate distally past the distal tip 145c of the latch 132 and engage actuation sled 115 in a manner as described above. Distal translation of slide 160 moves cam extension 162 of slide 160 out of engagement with cam feature 144 and allows latch 132 to move back to the locked-out configuration via the biasing force provided by leg portions 133a, 133b of the spring clip 131.

After the cartridge 112 has been fired, refraction of the drive member "D" will cause working end 101 to engage and pivot the latch 132 out of the path of the working end 101 such that drive member "D" will move proximally past latch 132 until working end 101 of the drive member "D" returns to the retracted configuration. In the retracted configuration, latch 132 is engaged within recess 116 such that distal tip 145c of latch 132 is positioned to engage back wall 119b of recess 116 to prevent further advancement of drive member "D," as described above.

The unique configuration of lock assembly 130 overcomes the aforementioned drawbacks that are, typically, associated with conventional surgical stapling apparatus. Specifically, lock assembly 130 prevents firing of a surgical stapling apparatus which does not have a cartridge 112 installed, or firing of a surgical stapling apparatus with a spent or empty cartridge 112 installed.

From the foregoing and with reference to the various figure drawings, those skilled in the art will appreciate that certain modifications can also be made to the present disclosure without departing from the scope of the same.

For example, with reference to FIGS. 15-19, an alternate embodiment of locking mechanism is illustrated. Accordingly, only those features that are unique to the embodiment illustrated in FIGS. 15-19 are described herein.

An anvil 211 includes a stop in the form of a notch 219 at a proximal end thereof that is configured to lock out a working end 201 of the drive member "D." Specifically, notch 219 is configured to engage a top flange 218a of working end 201 of the drive member "D" to prevent working end 201 from translating distally past notch 219.

A resilient member in the form of a wave spring 231 (or other suitable spring, e.g., coil, torsion, etc.) is operably coupled (e.g., via laser or electron welding) to an upper interior surface 223 of the jaw member 210. One or more other suitable coupling methods may also be utilized to couple spring 231 to interior surface 223. For example, adhesives, various mechanical interfaces and the like may be utilized to couple spring 231 to interior surface 223. Spring 231 is positioned proximal of notch 219 and is configured to contact a top flange 218a of working end 201 to bias flange 218a in a generally downwardly direction. Specifically, spring 231 biases top flange 218a into alignment with notch 219 such that distal translation of the working end 201 of the drive member "D" causes top flange 218a of working end 201 to engage the notch 219 on the anvil 211 to prevent further advancement of the drive member "D." In a compressed configuration, top flange 218a of the knife 205 will be positioned above notch 219 to allow further advancement of the drive member "D" through the cartridge.

A recess 216 is provided at a distal end of working end 201 adjacent a bottom flange 218b. Specifically, recess 216 is defined by a back wall 220 of working end 201 having a slanted configuration and is configured engage a corresponding protuberance in the form of a ramp 260 provided at a proximal end of the actuation sled 215. Engagement between recess 216 and ramp 260 raises top flange 218a above notch 219 against the biasing force of spring 231 to allow distal translation of working end 201 of the drive member "D" past notch 219.

Unlike actuation sled 115, actuation sled 215 is not configured to couple to a slide 160. Rather, ramp 260 extends proximally from the proximal end of actuation sled 215 and is positioned to engage back wall 220 of recess 216 when working end 201 of the drive member "D" is translated distally.

An indent/detent configuration (or other suitable mechanical interface) may be utilized to maintain actuation sled 215 in place while cartridge 212 is being installed on the jaw member (not shown for clarity purposes). In the embodiment illustrated in FIGS. 15-19, for example, an indent 240 (FIGS. 18-19) is provided on an interior bottom surface 242 of cartridge 212 and a corresponding detent 244 is provided on a bottom surface 246 of actuation sled 215 (FIGS. 15-17). Once knife 205 of the working end 201 contacts actuation sled 215, detent 244 releases from indent 240 and slides along interior bottom surface 242 with actuation sled 215.

In use, when cartridge assembly 212 is not installed on the jaw member, spring 231 is in a uncompressed state and configured to bias top flange 218a of the knife 205 in a manner as described above. With top flange 218a in the biased configuration, working end 201 of the drive member "D" is locked out and prevented from misfiring.

When cartridge 212 is installed on the jaw member, ramp 260 is positioned to engage recess 216 (FIGS. 15-16). Specifically, when the drive member "D" is advanced, ramp 260 of actuation sled 215 engages back wall 220 of recess 216 and raises top flange 218a of knife 205 above notch 219 on anvil 211 (FIG. 17) against the biasing force provided by spring 231. Spring 231 will remain in the compressed state until such time that ramp 260 is disengaged from recess 216. As a result thereof, drive member "D" is allowed to translate distally through cartridge 212 to staple and severe the stapled tissue (FIG. 18). Once top flange 218a of the working end 201 translates distally past notch 219, spring 231 will move back to the uncompressed configuration.

Working end 201 of the drive member "D" may then be moved proximally back to the retracted configuration. With the working end 201 in the retracted configuration, spring 231 will be in the uncompressed state for biasing top flange 218a of the knife 205 in a manner as described above to lock out the drive member "D" working end 201 and prevent firing of a surgical stapling apparatus which does not have a cartridge 212 installed, or firing of a surgical stapling apparatus with a spent or empty cartridge 112 installed.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical stapling apparatus, comprising:
   a housing;
   an elongated member extending from the housing;
   a tool assembly supported on a distal end of the elongated member, the tool assembly including a first jaw member and a second jaw member configured to move relative to each other between an open configuration and a closed configuration;
   a cartridge assembly including a plurality of staples, the cartridge assembly releasably supported on the first jaw member, the cartridge assembly including an actuation sled and a slide releasably coupled to the actuation sled;
   an anvil operably supported on the second jaw member;
   a drive member having a working end that is positioned and configured to translate through the first and second jaw members of the tool assembly when the first and second jaw members are in the closed configuration, the drive member being movable independently of the slide;
   a lock assembly including a latch movable from a locked position to an unlocked position, wherein in the locked position, the latch is positioned and configured to prevent distal translation of the drive member through the tool assembly; and
   a spring member positioned and configured to urge the latch towards the locked position wherein the slide is configured to move the latch from the locked position to the unlocked position upon installation of the cartridge assembly onto the first jaw member, the drive member moving the slide and the actuation sled distally upon actuation of the stapling apparatus, and in a distal configuration of the slide, the slide uncouples from the actuation sled and the spring member biases the latch to move to the locked position.

2. A surgical stapling apparatus according to claim 1, further including a pivot assembly, wherein the lock assembly is operably coupled to the pivot assembly.

3. A surgical stapling apparatus according to claim 2, wherein the lock assembly includes a cam pin configured to be contacted by the slide, the resilient member and at least one washer, and wherein the cam pin is positioned through an aperture defined through the pivot assembly, the cam pin being configured to rotate within the aperture to move the latch from the locked position to the unlocked position when the cam pin is contacted by the slide.

4. A surgical stapling apparatus according to claim 3, wherein the working end includes at least one recess that is configured to selectively engage the latch.

5. A surgical stapling apparatus according to claim 1, wherein the slide is configured to releasably couple to the actuation sled.

6. A surgical stapling apparatus according to claim 1, wherein the slide includes at least one mechanical interface that is configured to couple to a corresponding mechanical interface disposed within the cartridge assembly when the actuation sled is moved distally.

7. A surgical stapling apparatus according to claim 6, wherein the mechanical interfaces disposed on the slide and within the cartridge assembly form a dovetail joint.

8. A reload comprising:
   a tool assembly including a first jaw member and a second jaw member configured to move relative to each other between an open configuration and a closed configuration;
   a cartridge assembly releasably supported on the first jaw member, the cartridge assembly including an actuation sled and a slide releasably coupled to the actuation sled;
   an anvil supported on the second jaw member;
   a drive member having a working end configured to translate through the tool assembly when the first and second jaw members are in the closed configuration; and
   a lock assembly including a latch movable from a locked position to an unlocked position, wherein in the locked position, the latch is positioned and configured to prevent distal translation of the drive member through the reload,
   wherein the slide is configured to move the latch from the locked position to the unlocked position upon installation of the cartridge assembly onto the first jaw member, the slide being coupled to the actuation sled during installation of the cartridge assembly.

9. A reload according to claim 8, wherein the lock assembly is operably coupled to a pivot assembly of the reload.

10. A reload according to claim 9, wherein the lock assembly includes a cam pin configured to be contacted by the slide, at least one resilient member and at least one washer, and wherein the cam pin is positioned through an aperture defined through the pivot assembly, the cam pin being configured to rotate within the aperture to move the latch from the locked position to the unlocked position when the cam pin is contacted by the slide.

11. A reload according to claim 10, wherein the working end includes at least one recess that is configured to selectively engage the latch.

12. A reload according to claim 8, wherein the slide is configured to releasably couple to the actuation sled.

13. A reload according to claim 8, wherein the slide includes at least one mechanical interface that is configured to couple to a corresponding mechanical interface disposed within the cartridge assembly when the actuation sled is moved distally.

14. A reload according to claim 13, wherein the mechanical interfaces disposed on the slide and within the cartridge assembly form a dovetail joint.

* * * * *

UNITED STATES PATENT AND TRADEMARK OFFICE
CERTIFICATE OF CORRECTION

PATENT NO. : 9,717,498 B2  Page 1 of 1
APPLICATION NO. : 14/169463
DATED : August 1, 2017
INVENTOR(S) : Aranyi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 680 days.

Signed and Sealed this

Twenty-fifth Day of September, 2018

Andrei Iancu
*Director of the United States Patent and Trademark Office*